United States Patent [19]

Beecher

[11] Patent Number: 4,765,372
[45] Date of Patent: Aug. 23, 1988

[54] CHECK VALVE

[75] Inventor: William H. Beecher, Elmhurst, Ill.

[73] Assignee: Illinois Tool Works Inc., Chicago, Ill.

[21] Appl. No.: 505,501

[22] Filed: Jun. 17, 1983

[51] Int. Cl.<sup>4</sup> .............................................. F16K 15/14
[52] U.S. Cl. ...................................................... 137/843
[58] Field of Search .................... 137/512.15, 843, 852, 137/854–858

[56] References Cited

U.S. PATENT DOCUMENTS

| | | |
|---|---|---|
| 2,292,003 | 8/1942 | Yant et al. ........................ 137/512.15 |
| 3,807,445 | 4/1974 | McPhee ............................. 137/843 |
| 3,889,710 | 6/1975 | Brost ................................ 137/512.15 |
| 4,222,407 | 9/1980 | Ruschke et al. ................. 137/512.15 |
| 4,324,097 | 4/1982 | Schmitt et al. .................. 137/512.15 |
| 4,415,003 | 11/1983 | Paradis et al. ................... 137/843 |

Primary Examiner—Martin P. Schwadron
Attorney, Agent, or Firm—David I. Roche; Thomas W. Buckman

[57] ABSTRACT

A backflow check valve is disclosed. The valve comprises a housing, a biasable disk within the housing and a valve seat carried by the housing against which the disk is urgeable. The housing has a fluid inlet and a fluid outlet. The disk is preferably disposed transverse to a preselected direction of fluid flow through the housing for controlling fluid flow therethrough. The disk is urgeable against the seat for preventing fluid from flowing contrary to the preselected direction of flow. The housing includes means in the housing for biasly engaging therein opposite sides of the disk. The housing further includes means in the housing for biasly engaging the disk along a first pair of spaced opposite end portions and for biasly engaging the disk along a second pair of spaced opposite end portions. The housing preferably includes a blade carried within the housing; and the seat preferably describes a curved surface having a depression into which the blade is insertable for biasly engaging, between the seat and the blade, opposite sides of the first pair of disk end portions.

10 Claims, 3 Drawing Sheets

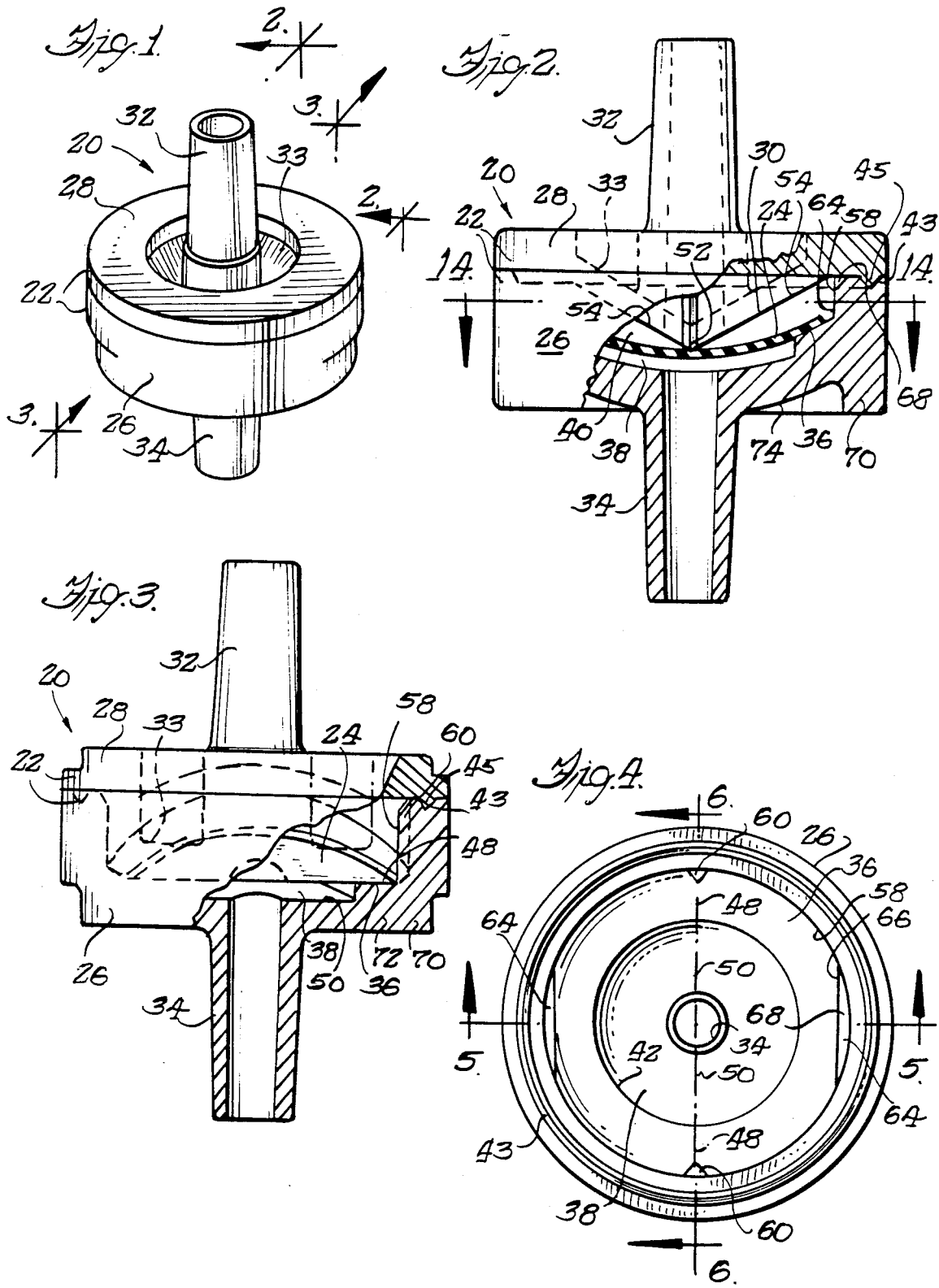

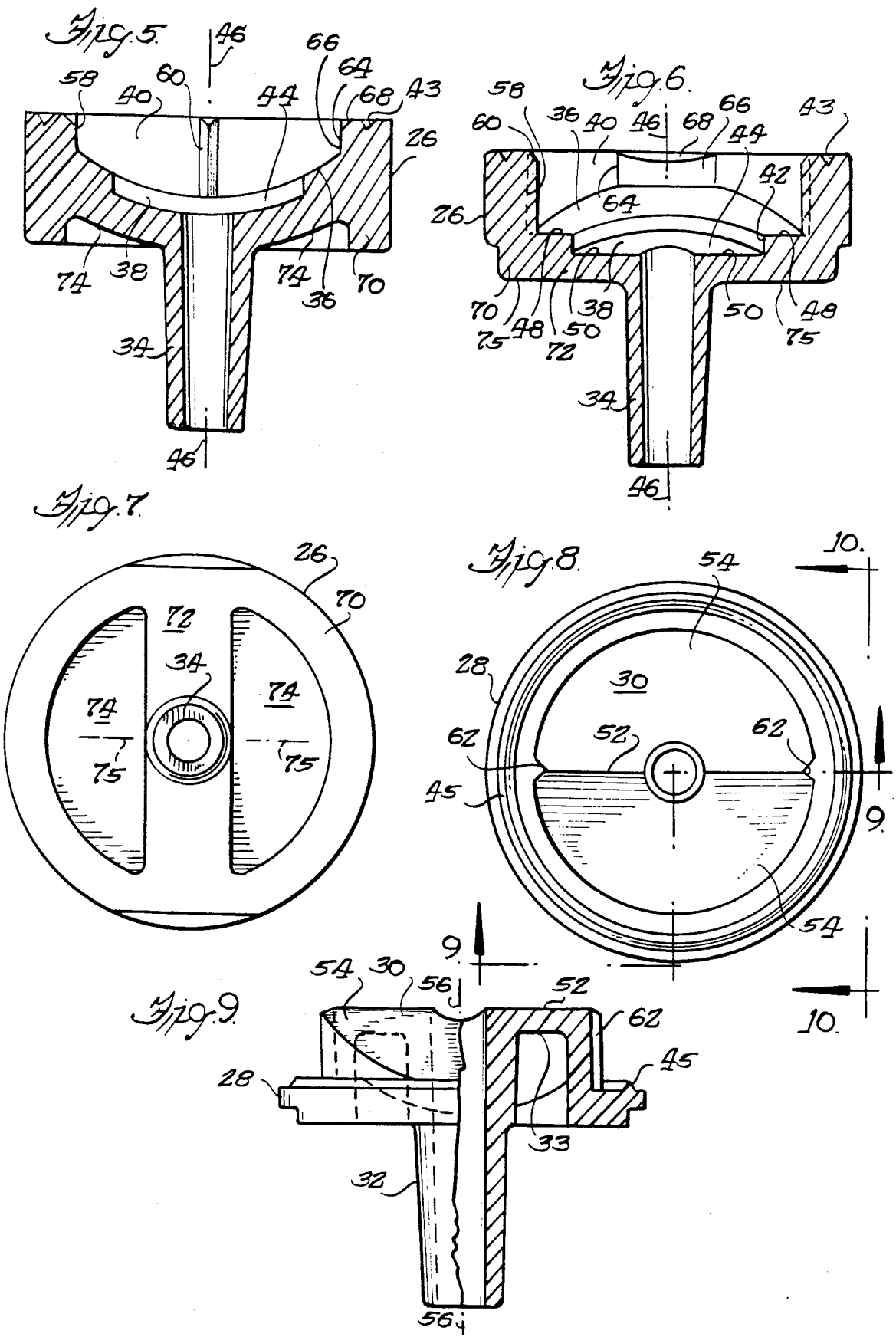

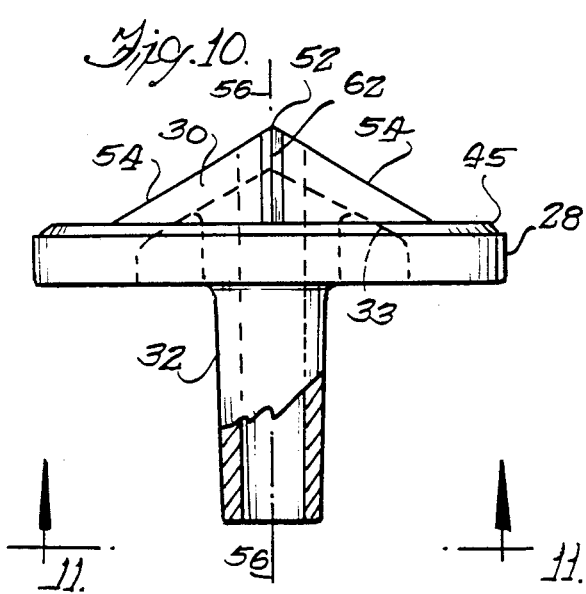
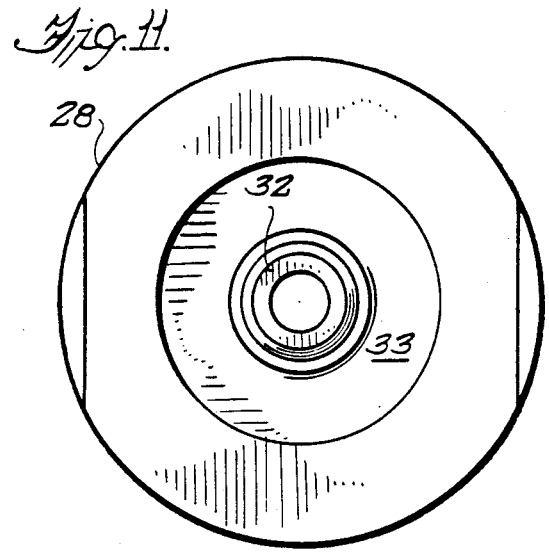
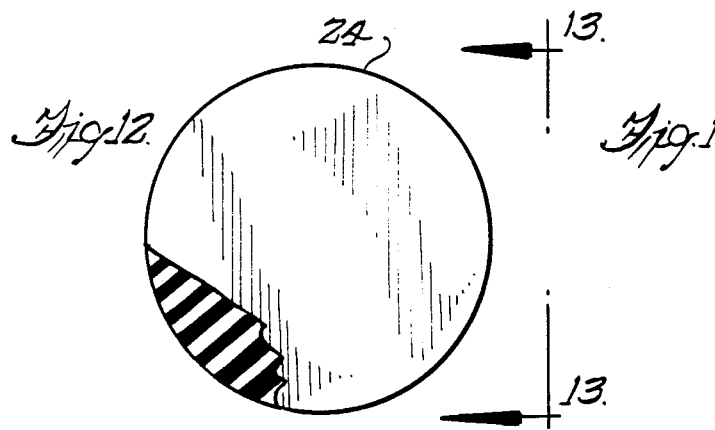
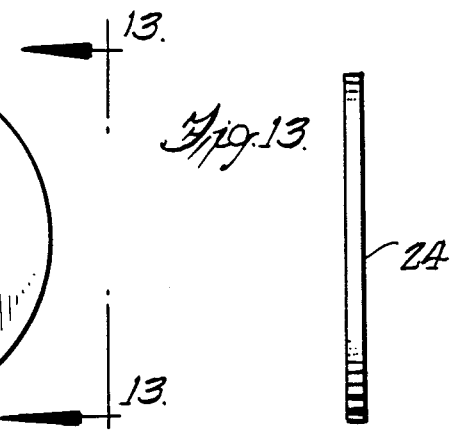
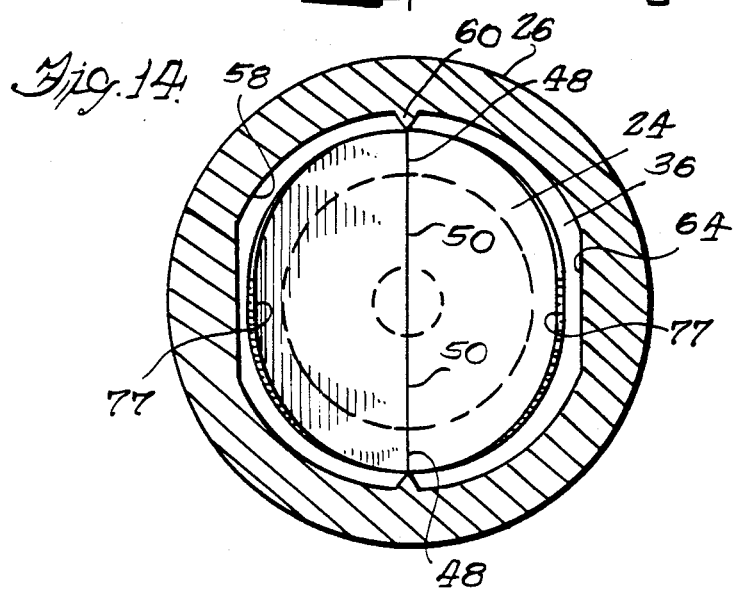

CHECK VALVE

BACKGROUND OF THE INVENTION

This invention is directed to a novel check valve. More particularly, this invention is directed to a backflow check valve for use with an intravenous (IV) administration set.

It has been observed that certain types of backflow check valves (such as those, for example, which are disclosed in the 2,292,003 patent to Yant et al, the 3,312,237 patent to Mon et al, and the 4,222,407 patent to Ruschke et al) wherein a disk or valve member is urged against a planar sealing surface, often develop leaks around the sealing surface. Because disks are usually cut from roll stock, they have a slight inherent curvature. Therefore, unless properly oriented, disks urged against a planar surface do not perform consistently.

As a result, some inventors have focused upon certain spatial relationships between the valve member and the sealing surface or seat. For example, in the 3,889,710 patent to Brost, it was thought essential that an abutment means be spaced from the sealing surface by more than the thickness of a disk. In the 4,354,492 patent to McPhee, another inventor thought it necessary that the valve member or disk against the valve seat be free of mechanical bias. In the 4,286,628 patent to Paradis et al, yet another inventor thought it necessary to employ prongs to pre-bias a flexible disk against a ring seat wherein flow check is achieved by engagement of the disk against a convex shoulder of the seat. For a variety of reasons, such backflow check valves also develop problems in IV use and must be replaced.

It has been observed, for example, that the use of a concave seating surface with a flotable disk is susceptible to malfunction because debris may become lodged in the concave portion of the disk. In addition, the disk may perform inconsistently depending upon its position upon the valve seat; in some positions the disk may have more flexural resistance than in others.

OBJECT AND SUMMARY OF THE INVENTION

Accordingly, it is a general object of this invention to provide a novel and improved backflow check valve.

A more specific object is to provide such a check valve having a housing of separable portions thereby permitting removal of the disk from the housing.

A further object is to provide such a check valve having a non-planar sealing surface.

Yet another object is to provide such a check valve wherein the check valve includes means in the housing for biasly engaging opposite sides of the disk.

Another object is to provide such a check valve which includes means for clamping the disk in place.

Briefly, and in accordance with the foregoing objects, a check valve according to the invention comprises a housing, a biasable disk within the housing and a valve seat carried by the housing against which the disk is urgeable. The housing has a fluid inlet and a fluid outlet. The disk is preferably disposed transverse to a preselected direction of fluid flow through the housing for controlling fluid flow therethrough. The disk is urged against the seat for preventing fluid from flowing contrary to the preselected direction of flow. The housing includes means in the housing for biasly engaging therein opposite sides of the disk. The housing further includes means in the housing for biasly engaging the disk along a first pair of spaced opposite end portions and for biasly engaging the disk along a second pair of spaced opposite end portions intermediate the first pair of disk end portions. The housing preferably includes a blade carried within the housing; and the seat preferably describes a curved surface having a depression into which the blade is insertable for biasly engaging between the seat and the blade opposite sides of the first pair of disk end portions.

BRIEF DESCRIPTION OF THE DRAWINGS

The foregoing, as well as other objects, features and advantages of the present invention will become more readily understood upon reading the following detailed description of the illustrated embodiment, together with reference to the drawings, wherein:

FIG. 1 is an isometric view of the novel backflow check valve;

FIG. 2 is a side view, partially in section, taken from the plane 2—2 in FIG. 1;

FIG. 3 is another side view, partially in section, taken generally from the plane 3—3 of FIG. 1;

FIG. 4 is a top view looking down into a female portion of the housing of the check valve;

FIG. 5 is a sectional view taken from the plane 5—5 of FIG. 4;

FIG. 6 is a sectional view taken from the plane 6—6 of FIG. 4;

FIG. 7 is a view of the underside of the female portion presented in FIG. 4;

FIG. 8 is a top view looking down onto a male portion of the check valve housing;

FIG. 9 is a side view, partially in section, taken along the lines 9—9 of FIG. 8;

FIG. 10 is a side view, partially in section, taken from the plane 10—10 of FIG. 8;

FIG. 11 is a bottom view of the male housing portion taken along the plane 11—11 of FIG. 10;

FIG. 12 is a top view of a disk member, partially in section, preferably biasly engageable between the male and female portions;

FIG. 13 is a side view of the disk taken from the plane 13—13 of FIG. 13; and

FIG. 14 is a top view of the disk as it is biasly urged by the male housing portion (not shown) into the female housing portion, the view of FIG. 14 having been taken along the plane 14—14 of FIG. 2.

DETAILED DESCRIPTION OF THE ILLUSTRATED EMBODIMENT

The novel backflow check valve 20 (FIG. 1) comprises a housing 22 and a valve member (preferably a disk) 24 (FIG. 2). The housing 22 preferably includes a cup or female portion 26 and a cover or male portion 28 having an integral blade 30 insertable into the cup 26. The female and male housing portions 26, 28 are both preferably circular in cross section (FIGS. 4 and 8).

The male portion 28 includes a centrally aligned (FIG. 11) and axially disposed (FIGS. 9 and 10) integral conduit 32 for obtaining substantially axial flow of fluid through the male portion 28. Circumferentially surrounding the conduit 32 and formed within the male housing portion 28 is an annular slot or recess 33 having an irregular floor (FIGS. 9 and 10) The conduit 32 preferably has a slight taper such that the outside diameter of the conduit 32 decreases progressively further away from the male portion 28.

The female portion 26 also preferably includes a centrally arranged (FIG. 7) and axially disposed (FIGS. 5 and 6) integral conduit 34 for obtaining substantially axial flow of fluid through the female portion 26. The female portion 26 further includes an integral seat 36 (FIGS. 4-6) against which the disk 24 is urgeable (FIG. 2) The female portion 26 also preferably includes a first recess or counterbore 38 intermediate the seat 36 and the conduit 34, and a second recess or cavity 40. The first recess or counterbore 38 is defined by a vertical sidewall 42 and a horizontally disposed curved surface or floor 44 (FIG. 6), both of which are integral with the female portion 26.

The male portion 28 covers the cavity 40 (FIGS. 2,3). An upper surface of the cup 26 includes an annular slot 43 (FIG. 4), preferably triangular in cross section (FIGS. 5,6); and the lower surface of the cover 28 includes a depending integral annular projections 45 (FIGS. 8-10) which is readily insertable into and which fits snugly in the cup slot 43 (FIGS. 2,3) for covering the cavity 40 in a fluid-tight manner.

The seat 36 and the surface or floor 44 are curved surfaces having irregular floors, each respectively preferably describing a cylindrical section having a depression disposed transverse to an axis 46 (FIGS. 5, 6) of the female portion 26. The seat 36 preferably has a nadir 48 (FIGS. 4,6); and the surface or floor 44 also preferably has seat nadir 48 (FIG. 4), but which is in a different plane (FIG. 6).

An edge 52 of the blade 30 is preferably formed from an intersection of two planar surfaces 54 (FIGS. 8-10). The blade edge 52 is preferably disposed transverse to an axis 56 of the male portion 28 (FIG. 9).

The second recess or cavity 40 (of the female portion 26) is defined by the seat 36 and a second vertical sidewall 58 (FIGS. 4-6). The first and second vertical sidewalls 42, 58 are preferably concentric to each other and to the conduit 34 (FIG. 4).

The female portion 26 also preferably includes ribs 60 integral with and radially inwardly projecting from the sidewall 58 (FIG. 4). The ribs 60 are axially disposed (FIG. 5) and oppositely spaced (FIG. 4) along the periphery of the sidewall 58.

The blade 30 preferably includes indentations 62 (FIGS. 8-10) axially disposed and oppositely spaced along the blade outer periphery for aligning the blade edge 52 with the nadir 48 of the seat 36.

The sidewall 58 (of the female portion 26) further includes a pair of integral projections 64 (FIGS. 4-6), one projection 64 being arranged on the sidewall 58 opposite the other projection 64 (FIG. 4), the projections 64 being intermediate the ribs 60. Each such projection 64 is defined by a planar surface 66, which is spaced from the axis 46 (FIGS. 5,6), and an inclined, concave surface 68 which is disposed inwardly toward the cavity 40.

The underside of the female portion 26 preferably includes a first integral rib 70 (FIGS. 5,7), radially disposed about the conduit 34, and a second integral rib 72, integral with the first rib 70 (FIG. 7), disposed transverse to the axis 46 (FIG. 6). The second rib 72 is integral with the conduit 34 and thereby provides structural support for the conduit 34 of the female portion 26.

The underside of the female portion 26 also includes two recesses 74 which are oppositely spaced from the conduit 34 (FIG. 7). Each of the recesses 74 preferably has a curvature defining a cylindrical section having a zenith 75 disposed transverse to the axis 46 (FIGS. 6, 7).

The disk 24 is preferably circular in cross section (FIG. 12). The disk 24 is relatively thin (FIG. 13); and is biasable and resilient. The preferred disk 24 is made of silicone rubber. The diameter of the disk 24 is such that when the disk 24 is urged against the seat 36 by the blade edge 52 (FIG. 2), the edge 52 contacting one side of the disk 24 to be urged against and to biasly engage the seat 36 along the seat nadir 48, and the curvature of the seat 36 causes the disk 24 to be biasly engaged by the seat 36 at spaced opposite end portions 77 (FIG. 14) of the disk 24. Such a biased engagement produces a uniform biasing in the disk 24 along the seat nadir 48 and transverse to the seat nadir 48 and thereby minimize shear stress in the disk 24. This is particularly important if low flow rates are desired. Since the disk is less stressed it allows very small amounts of fluid to flow through the valve. The disc can deflect more easily when held along a diameter than if biased into a partially spherical shape.

It is preferable that the distance between the interface of the male and female portions of the housing and the outer portions of the blade edge 52 is such that at least a portion of the blade edge clampingly engages and constantly squeezes outer portions the disk against the seat nadir 48. This clamping engagement may be very slight, but is important to assure that the disk is not free to slide to different positions on the valve seat 36.

Preferred direction of flow through the check valve 20 is into the conduit 34, through the first recess 38 and second recess 40 (fluid flow causing portions of the disk 24 to be lifted away from the seat 36) and out of the check valve 20 via the conduit 32 (FIG. 2). It can be appreciated, from the above discussion, that the disk 24, oppositely biasly engaged between the blade edge 52 and seat nadir 48, is positively positioned and thus preferably does not collapse into the recess 38. The prevention of collapse of the disk 24 into the recess 38 is aided by the fact that the disk is clamped between the blade edge 52 and the nadir 48.

The preferred geometry of the seat 36 will now be discussed. Referring to FIG. 14, it will be seen that the disk 24 is axially urged (preferably along a diameter thereof) by the blade 30 (not shown) against the nadir 48 of the seat 36. Referring to FIG. 6, it can be appreciated that the seat nadir 48 and axis 46 define a plane. A line perpendicular to this plane and passing through a point on the surface of the seat 36 defines a minimal distance from such point to the plane. Because the seat 36 is preferably a portion of a cylindrical section, the axial (FIG. 6) and radial (FIG. 5) curvature of the seat 36 (relative to the general predetermined direction of flow through the housing 22) causes the seat 36 to exert an increasingly biased pressure upon the underside of the disk 24 as this minimal dimension increases to a maximum at the disk end portions 77 (FIG. 14). This feature of the present invention insures leakless sealing of the disk 24 against the seat 36 for backflow check.

Also, because the disk 24 is respectively engaged on opposite sides by the blade edge 52 and seat nadir 48, it is not free to move axially; nor is the disk 24 free to move radially (relative to the axes 46, 56) within the housing 22.

Yet the elastomeric properties of the disk 24 are such that fluid flow, as above described, causes portions of the disk 24 to be lifted away from the seat 36; and the disk elastomeric and resiliency properties preferably do not prevent relatively small quantities of fluid from flowing from the first recess 38 into the second recess 40.

The ribs 60 and projections 64 preferably center (FIG. 4) the disk 24 in the recess or cavity 40, and preferably initially engage the disk 24. Engagement by the blade edge 52 (for causing the disk 24 to engage the seat 36) preferably causes the disk end portion 77 to be drawn away from the projections 64 approximately equally (FIG. 14). In the absence of fluid flow through the housing 22, upper and lower end portions of a diameter of the disk 24 are engaged by the blade edge 52 and the seat nadir 48 respectively, and the end portions 77, which are oppositely spaced from such diameter of the disk 24 are preferably engaged along an underside thereof by the seat 36.

As can be appreciated by those skilled in the art, the check valve 20 is capable of relatively high flow rate (in relation to free volume, available for fluid, within the housing 22). Moreover, because the blade 30 occupies a substantial portion of the second recess 40 and because the second recess 40 is relatively much greater in volume than the first recess 38, the volume of fluid needed to prime the check valve 20 is relatively low.

The housing 22 is preferably made of a commercially available molded thermoplastic carbonate-linked polymer. In the preferred embodiment, the female and male portions 26, 28 are preferably permanently secured together, such as by ultrasonic welding. Yet, it can be appreciated that, if desired, the female and male portions 26, 28 can be screwed together so that the disk 24 can be removed from the check valve 20 and another disk (not shown) having properties different from the disk 24 described above can be inserted in the check valve 20 for modifying fluid flow properties of the check valve 20. The cover 28 and cup 26 can, for example, accordingly respectively include meshing, integral, fluid-tight threaded portions for covering the cavity 40 in a fluid-tight manner.

Although the backflow check valve of the present invention has been disclosed as preferably being used in combination with IV administration sets, it can be appreciated, by those skilled in the art, that the present invention is generally useful as a check valve in a variety of applications (such as, for example, flow of liquids or gases) where backflow check is required.

What has been illustrated and described herein is a novel backflow check valve. While the check valve of the present invention has been illustrated and described with reference to a preferred embodiment, the invention is not limited thereto. On the contrary, alternatives, changes or modifications may become apparent to those skilled in the art upon reading the foregoing description. Accordingly, such alternatives, changes and modifications are to be considered as forming a part of the invention insofar as they fall within the spirit and scope of the appended claims.

I claim:

1. A backflow check valve comprising: a housing having a fluid inlet and a fluid outlet; a biasable disk carried within said housing disposed transverse to a preselected direction of fluid flow through said housing for controlling fluid flow through said housing; a valve seat carried by said housing against which said disk is biasly urgeable; and first and second disk-biasing means carried by said housing for biasly engaging said disk, at least one of said first and second disk-biasing means having an edge formed from two intersecting planar surfaces, the other one of said first and second disk-biasing means having a depression into which said edge is insertable for simultaneously engaging and respectively biasing opposite sides of said disk between said edge and said depression, said first and second disk-biasing means further including means carried by said housing for biasly engaging said disk along a first pair of spaced opposite end portions thereof and for biasly engaging said disk along a second pair of spaced opposite end portions thereof intermediate the first pair of disk end portions for preventing fluid from flowing contrary to said preselected direction of flow said second-biasing means including said valve seat and said depression, said valve seat being annular and said depression and said valve seat forming a concave cylindrical section, said section being cylindrical about an axis transverse to said direction of fluid flow, said section having a valley disposed transverse to said preselected direction of fluid flow.

2. The backflow check valve of claim 1 including means for clamping said disk to said seat.

3. The backflow check valve of claim 1 wherein said housing includes means integral therewith for aligning said edge with said valley.

4. A backflow check valve comprising: a housing having a fluid inlet and a fluid outlet, said housing including a female member having a cavity and further including a cover for said cavity, said cover having a male portion insertable into said cavity; a biasable disk engaged within said housing intermediate the cover male portion and the female member and disposed transverse to a preselected direction of fluid flow through said housing for controlling fluid flow through said housing; a valve seat integral with said female member against which said disk is biasly urgeable; and first and second disk-biasing means integral respectively with said cover and said female member for variably biasing said disk transverse to said direction of flow, at least one of said first and second disk-biasing means having an edge formed from two intersecting planar surfaces, the other one of said first and second disk-biasing means having a depression into which said edge is insertable for simultaneously engaging and respectively biasing opposite sides of said disk between said edge and said depression, said first and second disk-biasing means further including means carried by said housing for biasly engaging said disk along a first pair of spaced opposite end portions thereof and for biasly engaging said disk along a second pair of spaced opposite end portions thereof intermediate the first pair of disk end portions for preventing fluid from flowing contrary to said preselected direction of flow said second biasing means including said valve seat and said depression, said valve seat being annular and said depression and said valve seat forming a concave cylindrical section, said section being cylindrical about an axis transverse to said direction of fluid flow, said section having a valley disposed transverse to said preselected direction of fluid flow.

5. The backflow check valve of claim 6 including means for clamping said disk to said seat, said means for clamping including an axial relationship between said male portion and female member such that said disk is squeezed therebetween.

6. The backflow check valve of claim 4 including means carried by said housing for centering said disk in said cavity.

7. The backflow check valve of claim 6 wherein said disk and said cavity are circular in cross section, said disk having a smaller diameter than said cavity, and said housing includes means for centering said disk relative to said seat.

8. The backflow check valve of claim 2 wherein said cover and said female member include means for removably coupling said cover to said female member, said cover further including means for covering said cavity in a fluid-tight manner.

9. The backflow check valve of claim 7 wherein said valve seat further describes a generally annular surface having an irregular floor radially disposed about said preselected direction of fluid-flow, and said cover and said female member include means respectively integral therewith for aligning said edge with said valley.

10. The back flow check valve of claim 7 wherein said valve seat further describes a generally annular surface having an irregular floor radially disposed about said preselected direction of fluid-flow, and further including means integral with said female member for centering said disk relative to said seat.

* * * * *